(12) United States Patent
Stec et al.

(10) Patent No.: US 6,407,223 B1
(45) Date of Patent: Jun. 18, 2002

(54) PROCESS FOR THE SYNTHESIS OF MODIFIED P-CHIRAL NUCLEOTIDE ANALOGUES

(75) Inventors: Wojciech J. Stec, Ksawerów; Lucyna A. Woźniak, Lódź; Arkadiusz Chworoś, Hajnówka; Jaroslaw Pyzowski, Lódź, all of (PL)

(73) Assignee: Polska Akademia Nauk Cenirum Badan Molekularnych i Makromlekularnych, Lodz (PL)

( * ) Notice: Subject to any disclaimer, the term of this patent is extended or adjusted under 35 U.S.C. 154(b) by 0 days.

(21) Appl. No.: 09/402,974
(22) PCT Filed: Apr. 23, 1998
(86) PCT No.: PCT/PL98/00014
    § 371 (c)(1),
    (2), (4) Date: Oct. 14, 1999
(87) PCT Pub. No.: WO98/49179
    PCT Pub. Date: Nov. 5, 1998

(30) Foreign Application Priority Data

Apr. 25, 1997 (PL) .............................................. 9.319677

(51) Int. Cl.[7] .............................................. C07H 21/00
(52) U.S. Cl. ................ 536/25.3; 536/25.31; 536/25.32; 536/25.33; 536/25.34; 536/25.6; 536/26.26; 536/26.7; 536/26.71; 536/26.8
(58) Field of Search .............................. 536/25.3, 25.31, 536/25.32, 25.33, 25.34, 25.6, 26.26, 26.7, 26.71, 26.8

(56) References Cited

U.S. PATENT DOCUMENTS

| | | | | |
|---|---|---|---|---|
| 5,599,797 A | * | 2/1997 | Cook et al. |
| 5,635,488 A | * | 6/1997 | Cook et al. |
| 5,661,134 A | * | 8/1997 | Cook et al. |
| 5,852,188 A | * | 12/1998 | Cook |
| 5,856,465 A | * | 1/1999 | Stec et al. |
| 5,883,237 A | * | 3/1999 | Stec et al. |
| 5,945,521 A | * | 8/1999 | Just et al. |
| 5,955,597 A | * | 9/1999 | Arnold, Jr. et al. |
| 6,117,992 A | * | 9/2000 | Iyer |

FOREIGN PATENT DOCUMENTS

| | | |
|---|---|---|
| CA | 2205218 | 4/1997 |
| WO | 9607663 | 3/1996 |
| WO | 9637503 | 11/1996 |

OTHER PUBLICATIONS

Lesnikowski et al., Nucleic Acid Research, vol. 16, No. 24, pp. 11675–11689 (1988).*

Zain, R., et al. "Nucleoside H–phosphonates. Part 16. 31–P NMR studies on the transformation of nucleoside . . . " Joural of the Chemical Society Perkin Transactions 2(1996) pp 795–799.

Wang, Yu, et al. "Reactions of N–acylimidazole with nucleosides and nucleotides." Heteroc. vol. 28, No. 2 (1989) pp 592–601.

Lesnikowski, Z.J., et al. "Stereoselective synthesis of P–homochiral oligo . . . " Nucleic Acids Research, vol. 16, No. 24 (1988) pp 11675–11689.

Lesnikowski, Z.J., et al. "Stereospecific synthesis of (Sp) and (Sp)–Thymidyl (3',5') Thymidyl . . . " Tetrahedron Letters, vol. 28, No. 45 (1987) pp 5535–5538.

Garegg, P.J., et al. "Nucleoside H–phosphonates, IV. Automated solid phose synthesis of oligoribonucleotides . . . " Tetrahedron Letters, vol. 27, No. 34 (1986) pp4055–4058.

* cited by examiner

Primary Examiner—James O. Wilson
(74) Attorney, Agent, or Firm—Ladas & Parry

(57) ABSTRACT

The process of the instant invention is drawn to the synthesis of modified P-chiral nucleotide analogues in the form of pure diastereomers possessing preselected configuration at the P-atom. Oligonucleotides prepared by the method of the invention containing P-chiral compounds have enhanced hybridization and transporting properties.

23 Claims, 2 Drawing Sheets

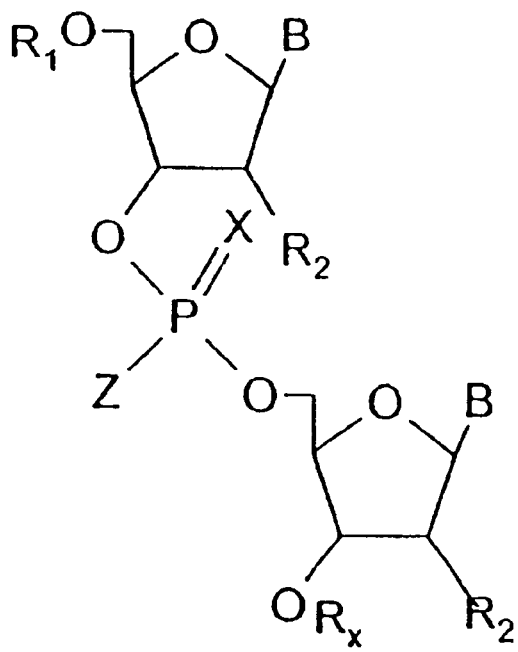
Formula 1
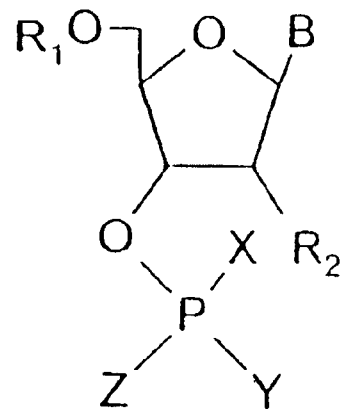
Formula 2
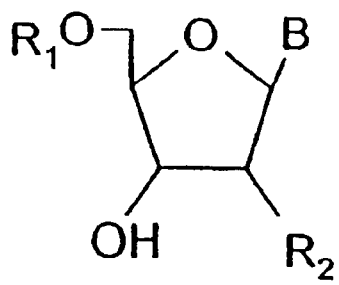
Formula 3
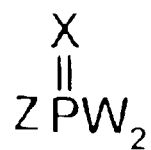
Formula 4

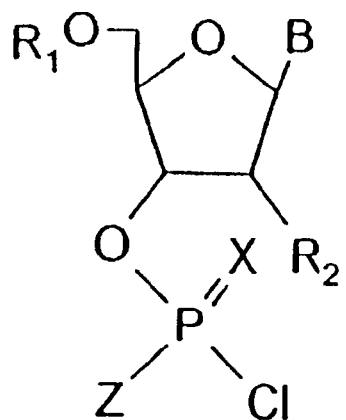
Formula 5
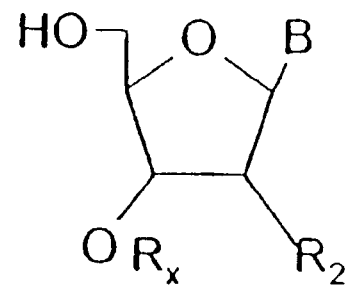
Formula 6
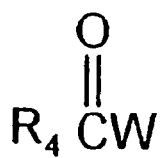
Formula 7
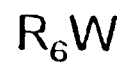
Formula 8

PROCESS FOR THE SYNTHESIS OF MODIFIED P-CHIRAL NUCLEOTIDE ANALOGUES

An object of the invention is to provide a process for the synthesis of modified P-chiral nucleotide analogues of general formula 1, where $R_1$ stands for protecting group, preferably 4,4'-dimethoxytrityl (DMT), 9-phenylxanthene-9-ol (Px) or trialkylsilyl group, $R_2$ is a hydrogen atom, protected hydroxyl group, halogen, chloroalkyl, nitrile, azide, protected amine, perfluoroalkyl (containing up to four carbon atoms), perfluoroalkoxyl (containing up to four carbon atoms and up to nine fluorine or chlorine atoms), alkoxyalkyl, vinyl, ethynyl, $OQ_1$, $SQ_1$, $NHQ_1$, where $Q_1$ stands for alkyl ($C_1$–$C_4$), aryl ($C_6$–$C_{12}$), alkenyl ($C_3$–$C_{12}$) or alkynyl ($C_3$–$C_{12}$), B stands for a purine or pyrimidine base (appropriately protected if necessary), Z is selected from $Q_1$ or vinyl, ethynyl, aminomethyl or aminoethyl substituents, X means oxygen, sulfur or selenium atom, $R_x$ is a protecting group, preferably aroyl, acyl, alkoxycarbonyl, benzenesulfonic, alkyl, trialkylsilyl group or the next unit of elongated oligonucleotide chain.

Bacterial or viral infection, as well as uncontrolled proliferation of cancer cells in a living organism, lead to a fully developed disease predominantly by synthesis of "unwanted", harmful proteins. Viral diseases result from incorporation of viral genetic information into a host's genome followed by synthesis of viral proteins, which are damaging to the host organism.

Caused by different factors aberrations of protooncogenes and formation of oncogenes responsible for synthesis of "unwanted" proteins are recognized as important factors in cancer cells proliferation processes.

Recent achievements in molecular biology, including explanation of molecular bases of such diseases as AIDS, different viral and cancer diseases or blood circulation disesaes, resulted in intensive search for new selective treatments aimed at inhibition of the expression of genes which code "unwanted" proteins, or at tuning of the level of known regulatory proteins.

Two newly developed therapeutic approaches are ANTI-SENSE mRNA (C. A. Stein, *Cancer Res.*, 1988, 48, 2659) and ANTIGENE (N. T. Thuong et al., *Angew.Chem.Int.Ed.Engl.*, 1993, 32) strategies, which stem from the knowledge on interactions between oligo (deoxyribonucleotide)s and DNA or RNA molecules. These conceptions are based on the assumption that short synthetic oligo(deoxyribonucleotide)s after being delivered inside a cell, form stable duplexes with complementary DNA or RNA molecules, and on this way slow down either transcription or translation process (E. Wickstrom, ed. Wiley-Liss, New York N.Y. 1993, "*Prospects for Antisense Nucleic Acid Therapy for Cancer and AIDS*").

Nucleolytic enzymes present in cells and body fluids are able to hydrolyze exogenous DNA molecules very rapidly, thus stability of oligo(deoxyribonucleotide)s and their analogues against nucleases is a crucial factor in respect to their in vivo activity. Majority of modifications introduced to the oligo(deoxyribonucleotide)s with the aim of their enhanced nucleolytic stability, involved changes of ligands attached to the phosphorus atom of the internucleotide phosphodiester bond. Among them phosphorothioate, methanephosphonate, phosphoramidate and triester analogues to various extent fulfill the criterion of full or, at least, significantly enhanced stability. However, such modifications usually result in reduced hybridization properties towards complementary DNA and RNA strands (J. S. Cohen, ed. *Oligonucleotides: Antisense Inhibitors of Gene Expression*, CRC Press, Inc., Boca Raton, Fla., 1989).

Applicability of antisense oligonucleotides as potential therapeutics depends upon their ability to cross the cellular membranes to reach necessary therapeutic concentration at the site of target molecules inside the cell (e.g. mRNA in cytoplasm). The cellular membranes made of protein-lipid layers are permeable only for small non-ionic molecules and are not permeable for most of natural metabolites and many drugs.

Natural and modified oligonucleotides complementary to fragments of viral DNA (RNA) are reported to show antiviral and anticancer properties in cell lines (in vivo), thus they are able to permeate through cell membranes and hybridize to the target DNA or RNA molecules. Several nucleolytically stable DNA analogues, as alkyl triesters (P. S. Miller, *Biochemistry*, 1977, 16, 1988), and methanephosphonates (C. H. Marcus-Sekura et al., *Nucleic Acids Res.*, 1987, 15, 5749; P. S. Miller et al., *Biochemistry*, 1986, 25, 5092; S. K. Loke et al., *Top. Microbiol. Immunol.*, 1988, 141, 282; A. M. Tari et al., *J.Biol.Med.*, 1996, 74, 623; S. Agrawal et al., *Clin.Pharmacokinet.*, 1995, 28, 7) were used for the research in different cell lines including human HL60, Syrian hamster fibroblasts, U 937, L 929, CV-1 and ATH 8. For modified oligonucleotides the cellular uptake is usually rather low, what results in reduced in vivo activity compared to that expected from in vitro studies.

So far, DNA analogues have worse hybridization properties than natural DNA, thus the inhibition of transcription or translation, and, consequently, inhibition of protein biosynthesis are less effective than expected. There are several reasons for this phenomenon, such as complicated third-order structure of RNA, limited accessibility of its particular segments, or DNA/RNA interactions with proteins.

In order to overcome these obstacles several DNA analogues possessing internucleotide linkages without phosphorus atom, like methylene group (M. Matteuci, *Tetrahedron Lett.*, 1990, 31, 2385) dialkylsilyl groups (R. Stirczak, *J.Org.Chem.*, 1987, 52, 202) or sulfonyl group (S. Benner, *J.Org.Chem.*, 1995, 61, 7620) have been synthesized. Research on their application as therapeutics is in an initial phase, mostly because of unfavorable physicochemical properties, as poor solubility and hybridization properties, and low chemical stability. Triester analogues are degradable by esterases, what renders them unusable in the antisense strategy (Goodrick et al., *Bioconj.Chem.*, 1990, 1, 165).

In the case of phosphorothioate and methanephosphonate analogues of DNA, which possess chiral center at the phosphorus atom, an additional problem is encountered, since the synthesis of oligomers with n internucleotide bonds results in formation of $2^n$ diastereoisomers, unless the method of synthesis is stereospecific.

It was found, that for oligo(nucleoside-3',5'-methanephosphonate)s of $R_P$-, $S_P$- or random configuration at each phosphorus atom, their hybridization properties towards complementary DNA or RNA depend on the configuration of the phosphorus centers (P. S. Miller et al., *J.Biol.Chem.*, 1980, 255, 9659; *Biochemistry*, 1982, 21, 2507). For phosphorothioate DNA analogues the stereodifferentiation of hybridization properties is accompanied by their stereoselective susceptibility to enzymatic hydrolysis by certain nucleases (Potter et al., *Biochemistry*, 1983, 22, 1369; Bryant et al., *Biochemistry*, 1979, 18, 2825).

Leśnikowski et al.(*Nucleic Acids Res.*, 1990, 18, 2109) found that stereospecifically synthesized octamer possessing six out of seven internucleotide methanephosphonate bonds of $R_P$ configuration has much stronger affinity towards pentadeoxyadenylic template than its counterpart possessing these bonds of $S_P$ configuration, or the oligomer obtained by non stereoselective method. The stereoregular oligomers were obtained by non stereoselective condensation of corresponding two stereoregular tetramers synthesized in solution starting from diastereomerically pure 5'-O-MMT-thymidine-3'-O-(O-p-nitrophenylmethanephosphonate)s and 3'-O-acetylthymidine with Grignard reagent used as an activator (Leśnikowski et al., *Nucleic Acids Res.,* 1990, 18, 2109; ibid, 1988, 16, 11675; Leśnikowski et al., *Nucleosides & Nucleotides,* 1991, 10, 773).

Other examples of synthesis of diastereomerically pure (or, at least, significantly enriched with an $R_P$ diastereoisomer) methanephosphonate analogues of DNA involve reactions of methyidichlorophosphine with appropriately protected at the 5' (first step) and 3' (second step) nucleosides, carried out at low temperature (−80° C.) in the presence of amines (including chiral amines). The highest obtained ratio of $R_P$ to $S_P$ isomers was 8:1 (Loscher, *Tetrahedron Lett.,* 1989, 30, 5587; Engels et al., *Nucleosides & Nucleotides,* 1991, 10, 347) This method allows to synthesize dinucleoside methanephosphonates in diastereoselective manner.

Another method for stereoselective formation of internucleotide methanephosphonate bond is a reaction employing separated diastereoisomers of 5'-O-DMT-N-protected nucleoside 3'-O-(Se-alkylmethanephosphonate)s and appropriate 3'-5'-OH-(N-protected) nucleosides in the presence of DBU and lithium chloride (Woźniak et al.,*J.Org.Chem.,* 1994, 58, 5061).

Recently, numerous laboratories have paid efforts to implement as therapeutics so called "chimeric" oligomers, possessing phosphate or phosphorothioate "core" flanked at both 5' and 3' ends by methanephosphonate units of $R_P$ configuration. The chimeras have enhanced stability against nucleases due to the presence of enzymatically stable internucleotide methanephosphonate linkages. Incorporation of methanephosphonate units only of $R_P$ configuration results in enhanced hybridization properties of the "chimeric" product (M. Reynolds et al., *Nucleic Acids Res.,* 1996, 24, 4584).

A process for the synthesis of modified P-chiral nucleotide analogues of general formula 1, where:

$R_1$ stands for protecting group, preferably 4,4'-dimethoxytrityl (DMT), 9-phenylxanthene-9-ol (Px) or trialkylsilyl group, $R_2$ is a hydrogen atom, protected hydroxyl group, halogen, chloroalkyl, nitrile, azide, protected amine, perfluoroalkyl (containing up to four carbon atoms), perfluoroalkoxyl (containing up to four carbon atoms and up to nine fluorine or chlorine atoms), alkoxyalkyl, vinyl, ethynyl, $OQ_1$, $SQ_1$, $NHQ_1$, where $Q_1$ stands for alkyl ($C_1$–$C_4$), aryl ($C_6$–$C_{12}$), alkenyl ($C_3$–$C_{12}$) or alkynyl ($C_3$–$C_{12}$), B stands for a purine or pyrimidine base (appropriately protected if necessary), Z is selected from $Q_1$ or vinyl, ethynyl, aminomethyl or aminoethyl substituents, X means oxygen, sulfur or selenium atom, and $R_x$ is a protecting group, preferably aroyl, acyl, alkoxycarbonyl, benzenesulfonic, alkyl, trialkylsilyl group or the next unit of elongated oligonucleotide chain according to the present invention, consists in reaction of compound of formula 2, where $R_1$, $R_2$, B and Z have the above mentioned meanings, while Y stands for $XR_3$ substituent, where X means oxygen, sulfur or selenium atom, and $R_3$ means acyl group of formula $COR_4$, in which $R_4$ stands for alkyl (up to six carbon atoms), perfluoroalkyl (containing up to four carbon atoms), aroyl (containing six up to fifteen carbon atoms), preferably mono-, di- or trisubstituted aromatic substituents (—$C_6H_4R_5$, —$C_6H_3(R_5)_2$ or—$C_6H_2(R_5)_3$, respectively), where $R_5$ means a hydrogen atom, methyl substituent, halogen atom or other substituent activating the aromatic ring, with compound of formula 6, where B, $R_2$ and $R_x$ have the above mentioned meanings, under anhydrous conditions, in an aprotic organic solvent, in the presence of an activating reagent, to yield compound of formula 1, which then is isolated, and if X means a sulfur or selenium atom compound of formula 1 is oxidized with known oxidizing reagents, preferably a mixture iodine/water/pyridine, hydrogen peroxide, alkyl hydroperoxides (preferably t-butyl hydroperoxide), or potassium peroxymonosulfate, followed by isolation of resulting 1 (where X means an oxygen atom and $R_1$, $R_2$, $R_x$, B and Z have the above mentioned meanings) using known methods. The process according to the present invention is carried out preferably in tetrahydrofuran or acetonitrile.

As an activating reagent in the reaction between compounds of formula 2 and formula 6 one can use organic bases, preferably amines, more preferably 1,8-diazabicyclo[5.4.0]undec-7-ene (DBU) or 1,5-diazabicyclo[4.3.0]non-5-ene (DBN).

In the process according to the present invention it is preferred to use an additional activator selected from a group consisting of lithium salts, especially lithium halides.

Another variant of the process for the synthesis of modified P-chiral nucleotide analogues of general formula 1 in the form of pure diastereomer of preselected configuration at the P-atom, where $R_1$, $R_2$, $R_x$, B, X and Z have the above mentioned meanings, according to the present invention consist in reaction of one of two diastereomers of compound of formula 2 of the configuration at the P-atom identical to that desired in the product, where $R_1$, $R_2$, B and X have the above mentioned meanings, while Y stands for $XR_3$ substituent, where X means an oxygen, sulfur or selenium atom, $R_3$ means acyl group of formula $COR_4$, in which $R_4$ stands for alkyl (up to six carbon atoms), perfluoroalkyl (containing up to four carbon atoms), aryl (containing six up to fifteen carbon atoms), including mono-, di- or tri-substituted aromatic substituents (—$C_6H_4R_5$, —$C_6H_3(R_5)_2$ or —$C_6H_2(R_5)_3$, respectively), where $R_5$ means a hydrogen atom, methyl substituent, halogen atom or other substituent activating the aromatic ring, with compound of formula 6, where B, $R_2$ and $R_x$ have the above mentioned meanings, under anhydrous conditions, in an aprotic organic solvent, in the presence of an activating reagent, to yield compound of formula 1, which then is isolated, or, if X means a sulfur or selenium atom, compound of formula 1 is oxidized with known oxidizing reagents, preferably a mixture iodine/water/pyridine, hydrogen peroxide, alkyl hydroperoxides (preferably t-butyl hydroperoxide), or potassium peroxymonosulfate, followed by isolation of resulting 1 (where X means an oxygen atom and $R_1$, $R_2$,$R_x$, B and Z have the above mentioned meanings) using known methods.

The process according to the present invention is carried out preferably in tetrahydrofuran or acetonitrile. As the activating reagent in the reaction between compounds of formula 2 and formula 6 one can use organic bases, preferably amines, more preferably 1,8-diazabicyclo[5.4.0]undec- 7-ene (DBU) or 1,5-diazabicyclo[4.3.0]non-5-ene (DBN), and as an additional activator compounds selected from a group consisting of lithium salts, especially lithium halides, can be used.

The third variant of the process for the synthesis of modified P-chiral nucleotide analogues of general formula 1 in the form of pure diastereomer of preselected configuration at the P-atom, where $R_1$, $R_2$, $R_x$, B, X and Z have the above mentioned meanings, according to the present invention consist in hydrolysis of one of two diastereomers of compound of formula 2 of the configuration at the P-atom opposite to that desired in the product of formula 1, while in the formula 2 $R_1$, $R_2$, B, Z, X and Y have the above mentioned meanings, in the presence of activator being able to invert an absolute configuration of the P-atom, while resulting product of general formula 2, where $R_1$, $R_2$, and B have the above mentioned meanings, while Y stands for an oxygen atom and X means a sulfur or selenium atom, is reacted with compound of general formula 7, where $R_4$ stands for alkyl (up to six carbon atoms), perfluoroalkyl (containing up to four carbon atoms), aroyl (containing six up to fifteen carbon atoms), including mono-, di- or tri-substituted aromatic substituents (—$C_6H_4R_5$, —$C_6H_3(R_5)_2$ or —$C_6H_2(R_5)_3$, respectively), where $R_5$ means a hydrogen atom, methyl substituent, halogen atom or any other substituent, and W means a chlorine, bromine or iodine atom, to yield compound of formula 2, where $R_1$, $R_2$, B and Z have the above mentioned meanings, X means a sulfur or selenium atom, while Y stands for $R_4C(O)O$—, in which $R_4$ has the above mentioned meaning, possessing the absolute configuration at the P-atom opposite to that in the starting material, and identical to that required for the product of formula 1, further possibly combined with the same diastereoisomer of formula 2 obtained from the earlier separation, and then reacted with compound of formula 6, where B, $R_2$ and $R_x$ have the above mentioned meanings, under anhydrous conditions, in an aprotic organic solvent, in the presence of an activating reagent, to yield compound of formula 1 of desired absolute configuration at the P-atom, which then is isolated, or, if X means a sulfur or selenium atom, compound of formula 1 is oxidized with known oxidizing reagents, preferably a mixture iodine/water/pyridine, hydrogen peroxide, alkyl hydroperoxides (preferably t-butyl hydroperoxide), or potassium peroxymonosulfate, followed by isolation of resulting 1 (where X means an oxygen atom and $R_1$, $R_2$, $R_x$, B and Z have the above mentioned meanings) using known methods. The process according to the present invention is carried out preferably in tetrahydrofuran or acetonitrile.

As an activating reagent in the reaction between compounds of formula 2 and formula 6 one can use organic bases, preferably amines, more preferably 1,8-diazabicyclo[5.4.0]undec-7-ene (DBU) or 1,5-diazabicyclo[4.3.0]non-5-ene (DBN) and as an additional activator lithium salts, especially lithium halides, are used.

The fourth variant of the process for the synthesis of modified P-chiral nucleotide analogues of general formula 1 in the form of pure diastereomer of preselected configuration at the P-atom, where $R_1$, $R_2$, $R_x$, B and Z have the above mentioned meanings, according to the present invention consist in reaction of one of two diastereomers of formula 2 of the configuration at the P-atom opposite to that desired in the product 1, while in the formula 2 $R_1$, $R_2$, B, Z, X and Y have the above mentioned meanings, with alcohol, preferably with methanol, possibly in the presence of activator, while the resulting product of general formula 2, where $R_1$, $R_2$, Z and B have the above mentioned meanings, while Y stands for an alkoxyl group, preferably methoxyl, and X means a sulfur or selenium atom, is further dealkylated using amines, preferably trimethylamine or t-butylamine, and the resulting compound of formula 2, where $R_1$, $R_2$, Z and B have the above mentioned meanings, while Y stands for an oxygen atom and X means a sulfur or selenium atom, is subsequently reacted with compound of general formula 7, where $R_4$ and W have the above mentioned meanings, to yield compound of formula 2, where $R_1$, $R_2$, Z and B have the above mentioned meanings, X means a sulfur or selenium atom, while Y stands for $R_4C(O)O$—, possessing the absolute configuration at the P-atom opposite to that in the starting material, and identical to that required for the product of formula 1, further possibly combined with the same diastereoisomer of formula 2 obtained from the earlier separation, and then reacted with compound of formula 6, where B, $R_2$ and $R_x$ have the above mentioned meanings, under anhydrous conditions, in an aprotic organic solvent, in the presence of an activating reagent, to yield compound of formula 1 of desired absolute configuration at the P-atom, which then is isolated, or, if X means a sulfur or selenium atom, compound of formula 1 is oxidized with known oxidizing reagents, preferably a mixture iodine/water/pyridine, hydrogen peroxide, alkyl hydroperoxides (preferably t-butyl hydroperoxide), or potassium peroxymonosulfate, followed by isolation of resulting 1 (where X means an oxygen atom and $R_1$, $R_2$, $R_x$, B and Z have the above mentioned meanings) using known methods. The process according to the present invention is carried out preferably in tetrahydrofuran or acetonitrile.

As an activating reagent in the solvolysis and in the reaction between compounds of formula 2 and formula 6 one can use organic bases, preferably amines, more preferably 1,8-diazabicyclo[5.4.0]undec-7-ene (DBU) or 1,5-diazabicyclo[4.3.0]non-5-ene (DBN) and as an additional activator lithium salts, especially lithium halides, are used.

In the process according to the present invention preferably used compounds are those of general formula 2, obtained by phosphorylation of corresponding substrates of general formula 3, where $R_1$, $R_2$ and B have the above mentioned meanings, with phosphorylating reagents of general formula 4, where Z and X have the above mentioned meanings, W means a halogen atom, preferably chlorine, followed by hydrolysis without isolation of the intermediate 5, to yield compounds of formula 2, where $R_1$, $R_2$, B, Z and X have the above mentioned meanings, and Y means an oxygen atom.

Using the first variant of the process according to the present invention, pure diastereoisomers of formula 2 are transformed separately to yield pure diastereoisomers of compound 1.

More useful variant of the process according to the present invention consist in the reaction of compound of formula 3, where $R_1$ and B have the above mentioned meanings, with compound of formula 4, where X means a sulfur or selenium atom and Z has above mentioned meanings, to yield compound of formula 5, where X means an oxygen, sulfur or selenium atom, which is then hydrolyzed to yield compound of formula 2 where $R_1$, $R_2$, Z and X have the above mentioned meanings and Y means an oxygen atom, and separated chromatographically into two diastereomers, followed by reaction with compound of formula 7, where $R_4$ stands for alkyl (up to six carbon atoms), perfluoroalkyl (containing up to four carbon atoms), aroyl (containing six up to fifteen carbon atoms), including mono-, di- or tri-substituted aromatic substituents (—$C_6H_4R_5$, —$C_6H_3(R_5)_2$ or —$C_6H_2(R_5)_3$, respectively), where $R_5$ means a hydrogen atom, methyl substituent, halogen atom or any other substituent activating an aromatic ring, and W means a halogen, preferably chlorine. One isomer is reacted with compound of formula 6, to yield stereospecifically compound of formula 2, where Y stands for $R_4C(O)O—$, in which $R_4$ has the above mentioned meaning. This isomer of 2 is reacted with compound of formula 6, where B, $R_2$ and $R_x$ have the above mentioned meanings, in the presence of an activating reagent as an organic base, preferably tertiary amine, more preferably 1,8-diazabicyclo[5.4.0]undec-7-ene (DBU). Diastereomerically pure compound of formula 1 is isolated using known methods. In the process according to the present invention the product 1 is oxidized with known oxidizing reagents, preferably a mixture iodine/water/pyridine, hydrogen peroxide, alkyl hydroperoxides (preferably t-butyl hydroperoxide), or potassium peroxymonosulfate, to yield product 1, where X means an oxygen atom and $R_1$, $R_2$, $R_x$, B and Z have the above mentioned meanings.

In this variant the second diastereoisomer of 2 ($Y=R_4C(O)O—$) is reacted with alcohol (preferably methanol), and without isolation of intermediary 2, where $R_1$, $R_2$, Z and B have the above mentioned meanings, while Y stands for an alkoxyl group, preferably methoxyl, and X means a sulfur or selenium atom, is further dealkylated using strong base, preferably organic base, most preferably amine. This diastereoisomer has an absolute configuration opposite to that of the substrate 2, thus within the described above process inversion of configuration at the P-atom in compound of formula 2 takes place. The described variant of the invention allows to obtain compound of formula 2 (Z=O, X=S, Se) in which absolute configuration at the phosphorus atom is 100% inverted, starting from 2 ($Y=R_4C(O)O—$) without isolation of intermediary 2 (Z=OMe, X=S, Se). It allows also to use both separated diastereomers of 2 (Y=O, X=S, Se) for synthesis of one diastereomer of the same compound of formula 2 of desired configuration at the P-atom via compound of formula 2 (X=S or Se, $Y=R_4C(O)O—$).

Within the next variant of the invention, one of the separated diastereomers of 2 (Y=O, X=S, Se) possessing an absolute configuration identical with that desired for the product 1, is alkylated with known alkylating reagents, preferably alkyl halides 8 of general formula $R_6W$, where $R_6$ stands for methyl, cyanomethyl, halogenoacyl, benzyl or aromatic ring substituted benzyl, while W means a chlorine, bromine or iodine atom. The resulting compound of formula 2, where a) $R_1$ stands for protecting group, preferably 4,4'-dimethoxytrityl (DMT), 9-phenylxanthene-9-ol (Px) or trialkylsilyl group, b) $R_2$ is a hydrogen atom, protected hydroxyl group, halogen, chloroalkyl, nitrile, azide, protected amine, perfluoroalkyl (containing up to four carbon atoms), perfluoroalkoxyl (containing up to four carbon atoms and up to nine fluorine or chlorine atoms), alkoxyalkyl, vinyl, ethynyl, $OQ_1$, $SQ_1$, $NHQ_1$, where $Q_1$ stands for alkyl ($C_1$–$C_4$), aryl ($C_6$–$C_{12}$), alkenyl ($C_3$–$C_{12}$) or alkynyl ($C_3$–$C_{12}$), c) B stands for a purine or pyrimidine base (appropriately protected if necessary), d) Z is selected from $Q_1$ or vinyl, ethynyl, aminomethyl or aminoethyl substituents, X means oxygen and Y means $SR_6$ or $SeR_6$, where $R_6$ has the above mentioned meaning, is reacted with compound of formula 6, where B stands for a purine or pyrimidine base (appropriately protected if necessary), and $R_x$ is a protecting group, preferably aroyl, acyl, alkoxycarbonyl, or the next unit of elongated oligonucleotide chain. This reaction is catalyzed by strong bases, preferably organic bases as 1,8-diazabicyclo[5.4.0]undec-7-ene (DBU). An additional activator of this process may be selected from a group consisting of lithium salts, preferably lithium halides, most preferably lithium chloride. The resulting compound of formula 1, where X means an oxygen atom and other substituents have the above mentioned meanings, is isolated using known methods. This product has the absolute configuration identical to that of the product 1 obtained by oxidation of compound of formula 1, where X means a sulfur or selenium atom.

The second diastereomer of of formula 2 (X=S, Se, Y=O) is acylated with compound of formula of formula 7, and then condensed with compound of formula 6 as in the second variant of the process.

The resulting compound of formula 1, where X means a sulfur or selenium atom is isolated using known methods, and oxidized using known oxidizing reagents, preferably a mixture iodine/water/pyridine, hydrogen peroxide, alkyl hydroperoxides (preferably t-butyl hydroperoxide), or potassium peroxymonosulfate, to yield compound 1, where X means an oxygen atom and $R_1$, $R_2$, $R_x$, B and Z have the above mentioned meanings.

This means, that described above variant of the invention allows, starting from both separated diastereoisomers of 2 (X=S, Se, Y=O) which are independently converted on two different ways (vide supra) to yield one diastereoisomer of the product 1 of desired absolute configuration at the P-atom, where X means an oxygen atom and other substituents have the above mentioned meanings.

The examples of the process according to the invention, not limiting its scope, are presented below.

EXAMPLES 1–8

General method for synthesis of compounds of formula 2 (Z=Me, X=S or Se, Y=O).

To the solution of compound of general formula 3 (1 mmol) in pyridine, compound of general formula 4 (Z=Me, X=S or Se) was added, and the reacting mixture was stirred for 15 min. Then water was added and the stirring was continued for 10 minutes. The mixture was evaporated to dryness under reduced pressure. The residue was dissolved in chloroform, washed twice with $NaHCO_3$aq. The organic layer was dried with known drying agents (e.g. magnesium sulfate) and concentrated under reduced pressure. The resulting crude product was purified and/or separated into diastereomeric species by means of column chromatography.

Appropriate fractions were collected and evaporated to yield colorless foam, and finally precipitated from a mixture of chloroform (or methylene chloride) and petroleum ether.

Selected experimental details are collected in Table 1

TABLE 1

| Examples | B | $R_z$ | $^{31}$P NMR* (ppm) | Yield (%) |
|---|---|---|---|---|
| 1 | T | H | 77.67; 77.34 | 92 |
| 2 | $^{Bz}$A | H | 78.33; 78.77 | 90 |
| 3 | $^{Bz}$C | H | 76.41; 77.00 | 93 |
| 4 | $^{ibu}$G | H | 78.28; 78.97 | 85 |
| 5 | U | OMe | 78.24; 77.96 | 90 |
| 6 | $A^{Bz}$ | OMe | 78.24; 78.39 | 83 |
| 7 | $C^{Bz}$ | OMe | 78.83; 79.54 | 85 |
| 8 | $G^{ibu}$ | OMe | 79.03; 79.15 | 80 |

*in $CDCl_3$, as pyridinium salts

EXAMPLES 9–17

General method for synthesis of compounds of formula 2 (Z=Me, X=S or Se, Y=O(CO)R$_4$).

To the solution of 1 mmol of compound of formula 2 (X=S, Y=O) in pyridine (5 mL) compound of formula 7 was added (2–3 mmol) and the reacting mixture was stirred at room temperature until the substrate disappeared (TLC control). The mixture was concentrated under reduced pressure and oil residue was dissolved in chloroform. Purification was done either by column chromatography or precipitation from a mixture chloroform/petroleum ether.

Selected experimental details are collected in Table 2.

TABLE 2

| Nr | B | R$_z$ | R$_4$ | X | $^{31}$P NMR | Yield (%)* |
|---|---|---|---|---|---|---|
| 9 | T | H | 2,4,6-trimetylphenyl | S | 91.6 | +98 |
| 10 | A$^{Bz}$ | H | " | S | 91.3 | +98 |
| 11 | C$^{Bz}$ | H | " | S | 91.8; 91.3 | +98 |
| 12 | G$^{ibu}$ | H | " | S | 91.8; 92.3 | 96 |
| 13 | U | OMe | " | S |  | +98 |
| 14 | A$^{Bz}$ | H | " | Se | 92.04**; 91.79 | +98 |
| 15 | C$^{Bz}$ | H | " | Se | 92.11***; 91.73 | +98 |
| 16 | T | H | 2,4,6-trichlorphenyl | S | 93.03; 93.12 | +98 |
| 17 | T | H | phenyl | S | 92.12; 92.25 | +98 |

*Yield assessed from $^{31}$P NMR
**J$_{P-Se}$ = 916 Hz
***J$_{P-Se}$ = 912 Hz

General method for synthesis of compounds of formula 2 (Z=Me, X=S or Se, Y=O, O-alkyl (methyl, ethyl))

To the solution of 2 (Z=Me, X=S or Se, Y=O(CO)R$_4$) (1 mmol) in dry acetonitrile, 5 mmol of DBU and 10–20 mmol of alcohol were added. After the reaction was complete, the reaction mixture was concentrated under reduced pressure to ⅓ of initial volume, diluted with chloroform and washed with water and NaHCO$_3$aq. The organic layer was dried, the solvents were evaporated under reduced pressure and the product was isolated by column chromatography on silica gel.

Conversion of compounds of formula 2 (Z=Me, X=S or Se, Y=O(CO)R$_4$) into compounds of formula 1 (Z=Me, X=S or Se).

The reacting mixture consisting of compound of formula 2 (Z=Me, X=S or Se, Y=O(CO)R$_4$) (1 mmol), compound 6 (5 mmol) and DBU (20 mmol) in anhydrous acetonitrile was stirred at room temperature in an atmosphere of inert gas for 24 h. The mixture was concentrated under reduced pressure, to the residue chloroform was added and the solution was extracted twice with 0.05 m solution of citric acid. The organic layer was dried with magnesium sulfate, concentrated and the product was isolated chromatographically on a silica gel column.

EXAMPLE 18

Substrate 2:
[R$_1$=DMT, B=Thy, R$_Z$=H, Z=Me, X=S, Y=OC(O)C$_6$H$_2$(CH$_3$)$_3$];
FAST-[S$_P$]: $^{31}$P NMR d: 91.6 ppm.
Product 2:
[R$_1$=DMT, B=Thy, R$_Z$=H, Z=Me, X=S, Y=OMe]
[S$_P$]: $^{31}$P NMR d: 100.3 ppm; diast.purity +99%; yield 92%

EXAMPLE 19

Substrate 2:
[R$_1$=DMT, B=Thy, R$_Z$=H, Z=Me, X=S, Y=OC(O)C$_6$H$_2$(CH$_3$)$_3$];
SLOW-[R$_P$]: $^{31}$P NMR d: 91.3 ppm.
Product 2:
[R$_1$=DMT, B=Thy, R$_Z$=H, Z=Me, X=S, Y=OMe]
[R$_P$): $^{31}$P NMR d: 99.6 ppm; diast.purity +99%; yield 92%

EXAMPLE 20

Substrate 2:
[R$_1$=DMT, B=Thy, R$_Z$=H, Z=Me, X=S, Y=OC(O)C$_6$H$_2$(CH$_3$)$_3$];
FAST-[S$_P$]: $^{31}$P NMR d: 91.6 ppm.
Product 2:
[Y=OEt] [S$_P$]: $^{31}$P NMR d: 101.3 ppm; diast.purity 92%; yield 95%

EXAMPLE 21

Substrate 2:
[R$_1$=DMT, B=Thy, R$_Z$=H, Z=Me, X=S, Y=OC(O)C$_6$H$_2$(CH$_3$)$_3$];
FAST-[S$_P$]: $^{31}$P NMR d: 91.6 ppm;
alcohol: NCCH$_2$CH$_2$OH
time: 12 hours.
Product 2:
[Y=O] [S$_P$]: $^{31}$P NMR d: 75.7 ppm; diast.purity 95%; yield 99%

EXAMPLE 22

Substrate 2:
[R$_1$=DMT, B=Thy, R$_Z$=H, Z=Me, X=S, Y=OC(O)C$_6$H$_2$(CH$_3$)$_3$];
FAST-[S$_P$]; $^{31}$P NMR d: 91.6 ppm;
reaction with water; analogous reaction conditions
Product 2:
[Y=O] [S$_P$]: $^{31}$P NMR d: 74.3 ppm; diast.purity 100%; yield 99%

EXAMPLE 23

Substrate 2:
[R$_1$=DMT, B=Thy, R$_Z$=H, Z=Me, X=S, Y=OC(O)C$_6$H$_2$(CH$_3$)$_3$];
SLOW-[R$_P$]; $^{31}$P NMR d: 91.3 ppm;
reaction with water, analogous reaction conditions.
Product 2:
[Y=O] [R$_P$]: $^{31}$P NMR d: 74.65 ppm; diast. Purity 100%; yield 99%

EXAMPLE 24

Using the substrate 2 (R$_1$=DMT, R$_2$=H, B=Thy, Y=OC(O)C$_6$H$_2$(CH$_3$)$_3$-SLOW-[R$_P$] (d $^{31}$P NMR 91.3 ppm, diastereomeric purity 99+%), and compound 6 (R$_x$=t-BuMe$_2$Si, R$_2$=H, B=Thy) the product 1 [Z=Me, X=S] FAST-[R$_P$] was obtained in 80% yield and of diastereomeric purity 91%, d$^{31}$P NMR 99.3 ppm.

EXAMPLE 25

Using the substrate 2 (R$_1$=DMT, R$_2$=H, B=Thy, Y=OC(O)C$_6$H$_2$(CH$_3$)$_3$-FAST-[S$_P$] (d $^{31}$P NMR 91.6 ppm), and compound 6 ($R_x$=t-BuMe$_2$Si, $R_2$=H, B=Thy) the product 1 [Z=Me, X=S] SLOW-[$S_P$] was obtained in 82% yield and of diastereomeric purity 90%, d$^{31}$P NMR 100.2 ppm.

General method for inversion of absolute configuration at the P-atom in compound of formula 2 [Z=Me, X=S or Se, Y=OC(O)R$_4$.

A substrate 2 [$R_1$=DMT, X=S or Se, Y=OC(O)R$_4$]-FAST-[$S_P$]] was dissolved in acetonitrile and methanol (3:1 v:v) containing DBU (20 fold excess) and the solution was stirred at room temperature for 4 h. The product 2 [$R_1$=DMT, X=S or Se, Y=OMe] after extraction and drying was reacted with compound 7 (R$_4$C(O)W), and the resulting product 2 [$R_1$=DMT, X=S or Se, Y=OC(O)R$_4$]-SLOW-[$R_P$]] was isolated and purified as described in examples 9–17.

EXAMPLE 26

Using the substrate 2 ($R_1$=DMT, B=Thy, X=S, Y=OC(O)C$_6$H$_2$(CH$_3$)$_3$-FAST-[$S_P$] (d$^{31}$P NMR 91.6 ppm), the product 2 ($R_1$=DMT, B=Thy, X=S, Y=OC(O)C$_6$H$_2$(CH$_3$)$_3$-SLOW-[$R_P$]) was obtained in 86% yield as assessed by $^{31}$P NMR (d $^{31}$P NMR 91.3 ppm).

EXAMPLE 27

Using the substrate 2 ($R_1$=DMT, B=Thy, X=S, Y=OC(O)C$_6$H$_2$(CH$_3$)$_3$-SLOW-[$R_P$] (d $^{31}$P NMR 91.3 ppm), the product 2 ($R_1$=DMT, B=Thy, X=S, Y=OC(O)C$_6$H$_2$(CH$_3$)$_3$-FAST-[$S_P$]) was obtained in 80% yield as assessed by $^{31}$P NMR (d $^{31}$P NMR 91.6 ppm).

What is claimed is:

1. A process for the synthesis of modified P-chiral nucleotide analogues of Formula 1:

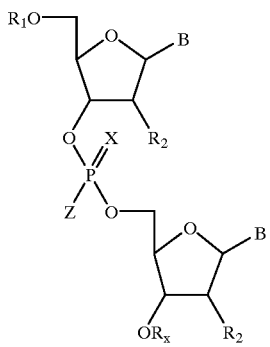

Formula 1 wherein:

$R_1$ is a protecting group;

$R_2$ is selected from hydrogen, protected hydroxyl group, vinyl, halogen, nitrile, azide, protected amine group, chloroalkyl, perfluoroalkyl, perfluoroalkoxyl, alkoxyalkyl, ethynyl, OQ$_1$, SQ$_1$, NHQ$_1$, where Q$_1$ stands for alkyl, aryl, alkenyl or alkynyl;

B is a purine or pyrimidine base;

Z is selected from alkyl, aryl, alkenyl, alkynyl, vinyl, ethynyl, aminomethyl or aminoethyl substituents;

X is an oxygen, sulfur or selenium atom;

$R_x$ is a protecting group;

said process comprising the steps of:

(a) providing the following compound of Formula 2:

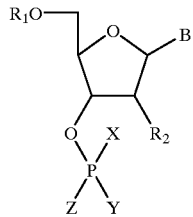

Formula 2 wherein $R_1$, $R_2$ and B are as defined above;

Y is an XR$_3$ substituent, wherein X is an oxygen, sulfur or selenium atom and R$_3$ is an acyl group of formula COR$_4$, in which R$_4$ is an alkyl group, perfluoroalkyl group, or an aryl substituent containing six to fifteen carbon atoms and having an aromatic ring comprising mono-, di- or tri-substituted aromatic substituents activating the aromatic ring;

(b) providing the following compound of Formula 6:

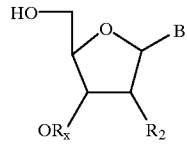

Formula 6 wherein:

B, $R_2$ and $R_x$ are as defined above;

(c) reacting the compound of Formula 6 with the compound of Formula 2 under anhydrous conditions, in an aprotic organic solvent, in the presence of at least one activating reagent, to yield the compound of Formula 1; and (d) isolating the compound of Formula 1.

2. The process according to claim 1, wherein $R_x$ is selected from aroyl, acyl, alkoxycarbonyl, benzenesulfonic, alkyl, trialkylsilyl group and an elongated oligonucleotide chain.

3. The process according to claim 1, wherein X is a sulfur or selenium atom and the process comprises oxidizing the compound of formula 1 with an oxidizing reagent, prior to the step of isolating the compound of Formula 1.

4. The process according to claim 1, wherein X is an oxygen atom.

5. The process according to claim 1, wherein the compound of Formula 2 is obtained by:

(i) phosphorylating with a phosphorylating reagent, a substrate of Formula 3:

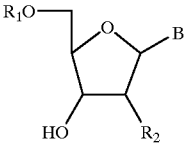

Formula 3 wherein $R_1$, $R_2$ and B are as defined previously, said phosphorylating reagent comprising a compound of Formula 4:

Formula 4

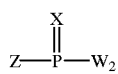

wherein:

Z is as defined previously, and W is a halogen; and (ii) followed by hydrolysis without isolation of the intermediate of Formula 5:

Formula 5

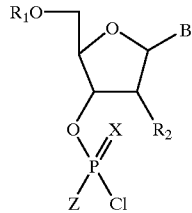

where $R_1$, $R_2$, B, Z and X are as defined in claim 1, and Y is an oxygen atom, to yield the compound of Formula 2.

6. The process according to claim 1, wherein the aprotic organic solvent comprises tetrahydrofuran or acetonitrile.

7. The process according to claim 1, wherein the at least one activating reagent is an organic base amine.

8. The process according to claim 1, wherein the reacting in step (c) comprises an additional activating reagent which is a lithium salt.

9. The process according to claim 1, wherein the compound of Formula 2 is a diastereoisomer which possesses an absolute configuration at the P-atom identical with that desired the analogues of Formula 1, said diastereoisomer being reacted with the compound of Formula 6 under anhydrous conditions, in the aprotic organic solvent, in the presence of the at least one activating reagent, to yield the compound of Formula 1.

10. The process according to claim 9, wherein the compound of Formula 2 is obtained by phosphorylation of a substrate of Formula 3:

Formula 3

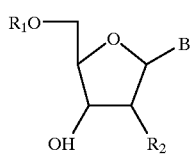

with a phosphorylating reagent of Formula 4:

Formula 4

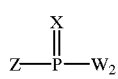

followed by hydrolysis without isolation of an intermediate of Formula 5:

Formula 5

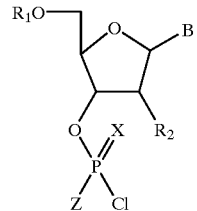

to yield a compound of Formula 2 wherein $R_1$, $R_2$, B, Z and X are as defined previously, and Y is an oxygen atom.

11. The process according to claim 9, wherein the aprotic organic solvent is tetrahydrofaran or acetonitrile.

12. The process according to claim 9, wherein the at least one activating reagent is an organic base.

13. The process according to claim 9, wherein the reacting in step (c) is in the presence of an additional activating reagent which is a lithium salt.

14. A process for the synthesis of modified P-chiral nucleotide analogues of Formula 1 in the form of a pure diastereoisomer possessing a preselected configuration at the P-atom:

Formula 1

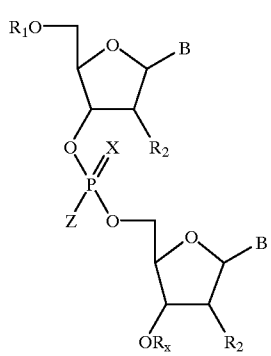

wherein:

$R_1$ is a protecting group;

$R_2$ is selected from hydrogen, protected hydroxyl group, vinyl, halogen, nitrile, azide, protected amine group, chloroalkyl, perfluoroalkyl, perfluoroalkoxyl, alkoxyalkyl, vinyl, ethynyl, $OQ_1$, $SQ_1$, $NHQ_1$, where $Q_1$ stands for alkyl, aryl, alkenyl or alkynyl;

B is a purine or pyrimidine base;

Z is selected from alkyl, aryl, alkenyl, alkynyl, vinyl, ethynyl, aminomethyl or aminoethyl substituents;

$R_x$ is a protecting group;

Y is an $XR_3$ substituent, where X is an oxygen, sulfur or selenium atom and $R_3$ is an acyl group of formula $COR_4$, in which $R_4$ is an alkyl group, perfluoroalkyl group, or an aryl substituent containing six to fifteen carbon atoms and having an aromatic ring comprising mono-, di- or tri-substituted aromatic substituents activating the aromatic ring; said process comprising the steps of:

(a) hydrolyzing a diastereoisomer of the compound of Formula 2:

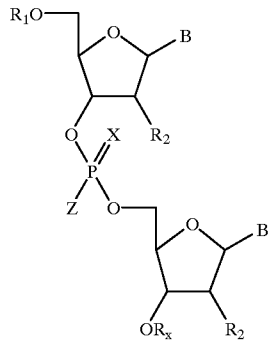

Formula 1 wherein:

$R_1$ is a protecting group;

$R_2$ is selected from hydrogen, protected hydroxyl group, vinyl, halogen, nitrile, azide, protected amine group, chloroalkyl, perfluoroalkyl, perfluoroalkoxyl, alkoxyalkyl, vinyl, ethynyl, $OQ_1$, $SQ_1$, $NHQ_1$, where $Q_1$ stands for alkyl, aryl, alkenyl or alkynyl;

B is a purine or pyrimidine base;

Z is selected from alkyl, aryl, alkenyl, alkynyl, vinyl, ethynyl, aminomethyl or aminoethyl substituents;

$R_x$ is a protecting group;

Y is an $XR_3$ substituent, where X is an oxygen, sulfur or selenium atom and $R_3$ is an acyl group of formula $COR_4$, in which $R_4$ is an alkyl group, perfluoroalkyl group, or an aryl substituent containing six to fifteen carbon atoms and having an aromatic ring comprising mono-, di- or tri-substituted aromatic substituents activating the aromatic ring; said process comprising the steps of:

(a) hydrolyzing a diastereoisomer of the compound of Formula 2:

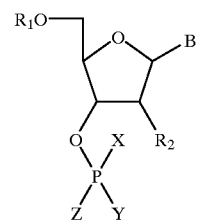

Formula 2 wherein:

$R_1$, $R_2$ and B are as defined above;

Y is an oxygen;

X is a sulfur or selenium atom, wherein the compound of Formula 2 possesses an absolute configuration at the P-atom opposite to that desired for the analogues of Formula 1, said hydrolyzing being done in the presence of an activator that inverts the absolute configuration of the P-atom resulting in a product of Formula 2, (b) reacting the product of step (a) with a compound of Formula 7:

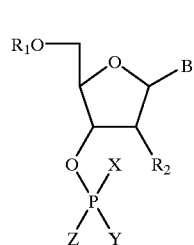

Formula 2 where:

$R_1$, $R_2$ and B are as defined above;

Y is an oxygen;

X is a sulfur or selenium atom, wherein the compound of Formula 2 possesses an absolute configuration at the P-atom opposite to that desired for the analogues of Formula 1, said hydrolyzing being done in the presence of an activator that inverts the absolute configuration of the P-atom resulting in a product of Formula 2, (b) reacting the product of step (a) with a compound of Formula 7:

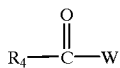

Formula 7 wherein $R_4$ is an alkyl, perfluoroalkyl, or a aroyl substituent containing six to fifteen carbon atoms, and having an aromatic ring comprising mono-, di- or tri-substituted aromatic substituents activating the aromatic ring; and W is a chlorine, bromine or iodine atom;

to yield the compound of Formula 2, where $R_1$, $R_2$, B and Z are as defined above, X is a sulfur or selenium atom, and Y is $R_4C(O)O-$, in which $R_4$ is as defined above, wherein the compound of Formula 7 possesses an absolute configuration at the P-atom opposite to that of the diastereoisomer of Formula 2, and identical to that which is desired for the analogues of Formula 1.

15. The process according to claim 14, wherein $R_x$ is selected from aroyl, acyl, alkoxycarbonyl, benzenesulfonic, alkyd, trialkylsilyl group and an elongated oligonucleotide chain.

16. A process for the synthesis of modified P-chiral nucleotide analogues of Formula 1 in the form of a pure diastereoisomer possessing a preselected configuration at the P-atom:

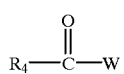

Formula 7 wherein

R$_4$ is an alkyl, perfluoroalkyl, or a aroyl substituent containing six to fifteen carbon atoms, and having an aromatic ring comprising mono-, di- or tri-substituted aromatic substituents activating the aromatic ring; and W is a chlorine; bromine or iodine atom, to yield the compound of Formula 2, where R$_1$, R$_2$, B and Z are as defined above, X is a sulfur or selenium atom, and Y is R$_4$C(O)O—, in which R$_4$ is as defined above, wherein the compound of Formula 7 possesses an absolute configuration at the P-atom opposite to that of the diastereoisomer of Formula 2, and identical to that which is desired for the analogues of Formula 1; and (c) reacting the product with compound of Formula 6:

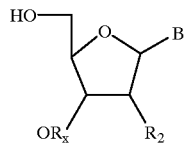

Formula 6 wherein

B, R$_2$ and R$_x$ are as defined previously, under anhydrous conditions, in an aprotic organic solvent, in the presence of an activating reagent, to yield the compound of Formula 1 and isolating the compound of Formula 1.

17. The process according to claim 14, wherein the compound of Formula 2 is obtained by:

(i) phosphorylating with a phosphorylating reagent, a substrate of Formula 3:

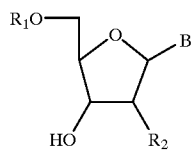

Formula 3 wherein

R$_1$, R$_2$ and B are as defined previously; said phosphorylating reagent comprising a compound of Formula 4:

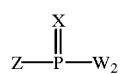

Formula 4 wherein

Z and X are as defined previously,

W is a halogen;

(ii) followed by hydrolysis without isolation of the intermediate of Formula 5:

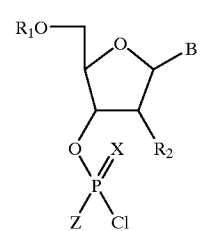

Formula 5 where

R$_1$, R$_2$, B, Z and X are defined previously, and Y is an oxygen atom to yield the compound of Formula 2.

18. The process according to claim 17, further comprising:

(i) separating chromatographically the compound of Formula 2 into two diastereoisomers: and (ii) reacting the diasterosiomer with compound of Formula 7:

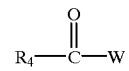

Formula 7 wherein:

R$_4$ is an alkyl group, perfluoroalkyl group, or an aroyl substituent containing six to fifteen carbon atoms and having an aromatic ring comprising mono-, di- or tri-substituted aromatic substituents activating the aromatic ring, and W is a halogen.

19. The process according to claim 14, wherein the activator is an organic base amine.

20. The process according to claim 14, wherein the aprotic organic solvent is tetrahydrofuran.

21. The process according to claim 16, wherein the activating reagent is a lithium salt.

22. A process for the synthesis of modified P-chiral nucleotide analogues of Formula 1 in the form of a pure diastereoisomer possessing a preselected configuration at the P-atom:

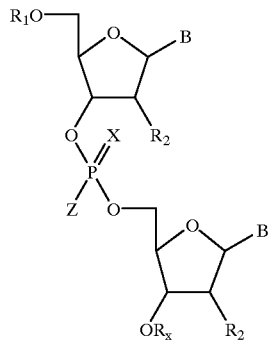

Formula 1 wherein:

R$_1$ is a protecting group;

R$_2$ is selected from hydrogen, protected hydroxyl group, vinyl, halogen, nitrile, azide, protected amine group, chloroalkyl, perfluoroalkyl, perfluoroalkoxyl, alkoxyalkyl, vinyl, ethynyl, OQ$_1$, SQ$_1$, NHQ$_1$, where Q$_1$ stands for alkyl, aryl, alkenyl or alkynyl;

Y is an oxygen;

X is a sulfur or selenium atom wherein the compound of Formula 2 possesses an absolute configuration at the P-atom opposite to that desired for the analogues of Formula 1, comprising the steps of:

(a) hydrolizing one of two diastereoisomers of formula 2 in the presence of an activator that inverts the absolute configuration of the P-atom resulting in a product of Formula 2

Formula 2

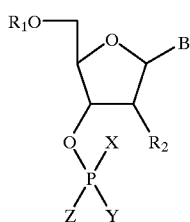

(b) reacting the product of step (a) with a compound of Formula 7:

Formula 7

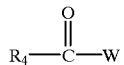

wherein

R$_4$ is an alkyl, perfluoroalkyl, or a aroyl substituent containing six to fifteen carbon atoms, and having an aromatic ring comprising mono-, di- or tri-substituted aromatic substituents activating the aromatic ring; and W is a chlorine, bromine or iodine atom, to yield the compound of Formula 2, where R$_1$, R$_2$, B and Z are as defined above, X is a sulfur or selenium atom, and Y is R$_4$C(O)O—, in which R$_4$ is as defined above, wherein the compound of Formula 7 possesses an absolute configuration at the P-atom opposite to that of the diastereoisomer of Formula 2, and identical to that which is desired for the analogues of Formula 1; and (c) providing the following compound of Formula 6:

Formula 6

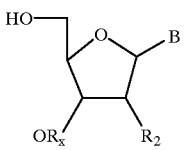

wherein

B, R$_2$ and R$_x$ are as defined previously;

(d) reacting the compound of Formula 6 with the compound of Formula 2 under anhydrous conditions, in an aprotic organic solvent, in the presence of an activating reagent, to yield compound of Formula 1 of desired absolute configuration at the P-atom; and (e) isolating the compound of Formula 1.

23. The process according to claim 14, wherein X is an oxygen, sulfur or selenium atom, and Y of Formula 2 is R$_4$C(O)O—.

* * * * *